US008864667B2

(12) United States Patent
Asao et al.

(10) Patent No.: US 8,864,667 B2
(45) Date of Patent: Oct. 21, 2014

(54) BIOLOGICAL INFORMATION IMAGING APPARATUS AND BIOLOGICAL INFORMATION IMAGING METHOD

(75) Inventors: Yasufumi Asao, Atsugi (JP); Kazuhiko Fukutani, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 649 days.

(21) Appl. No.: 12/544,834

(22) Filed: Aug. 20, 2009

(65) Prior Publication Data

US 2010/0049049 A1 Feb. 25, 2010

(30) Foreign Application Priority Data

Aug. 20, 2008 (JP) ................................. 2008-211993

(51) Int. Cl.
*A61B 8/00* (2006.01)
*A61B 5/00* (2006.01)
(52) U.S. Cl.
CPC ............. *A61B 5/0073* (2013.01); *A61B 5/7257* (2013.01); *A61B 5/0095* (2013.01)
USPC ............................ 600/437; 600/443; 600/476
(58) Field of Classification Search
USPC ......................................... 600/437, 443, 476
See application file for complete search history.

(56) References Cited

U.S. PATENT DOCUMENTS

| 5,070,733 | A  | * | 12/1991 | Nagata et al. ................... 73/602 |
| 7,515,948 | B1 | * | 4/2009  | Balberg et al. ................ 600/323 |
| 2008/0188724 | A1 | * | 8/2008 | Hwang et al. ................. 600/316 |
| 2008/0306371 | A1 |   | 12/2008 | Fukutani et al. .............. 600/407 |
| 2009/0002685 | A1 |   | 1/2009 | Fukutani et al. ................ 356/72 |
| 2009/0105605 | A1 | * | 4/2009 | Abreu ........................... 600/549 |
| 2009/0198128 | A1 |   | 8/2009 | Fukutani et al. .............. 600/437 |
| 2009/0227997 | A1 | * | 9/2009 | Wang et al. ..................... 606/10 |
| 2010/0049044 | A1 | * | 2/2010 | Burcher ........................ 600/437 |

FOREIGN PATENT DOCUMENTS

| JP | 62-189054      | 8/1987  |
| JP | H04-208143     | 7/1992  |
| JP | H11-004826     | 1/1999  |
| JP | 2002-045361    | 2/2002  |
| JP | 2006-521869    | 9/2006  |
| WO | WO 2004/086965 | 10/2004 |
| WO | WO 2006/111939 | 10/2006 |
| WO | WO 2008/075299 | 6/2008  |
| WO | WO 2009/001913 | 12/2008 |

OTHER PUBLICATIONS

Office Action issued Sep. 3, 2013 in counterpart Japanese patent application JP2008-211993, with translation.

* cited by examiner

*Primary Examiner* — Unsu Jung
*Assistant Examiner* — Daniel Huntley
(74) *Attorney, Agent, or Firm* — Fitzpatrick, Cella, Harper & Scinto

(57) ABSTRACT

A biological information imaging method includes a first measurement step to measure an acoustic wave (54) generated by light (53) which is irradiated to a living body (51) from a light source (50) and which is absorbed by tissue (52) in the living body, a storage step to store first information obtained in the first measurement step, a second measurement step to measure an acoustic wave (54) generated by light (53) which is irradiated to the living body (51) from the light source (50) and which is absorbed by the tissue (52) in the living body, and a processing step to generate an image of information of the tissue in the living body by using second information obtained in the second measurement step, and the first information stored in the storage step.

9 Claims, 11 Drawing Sheets

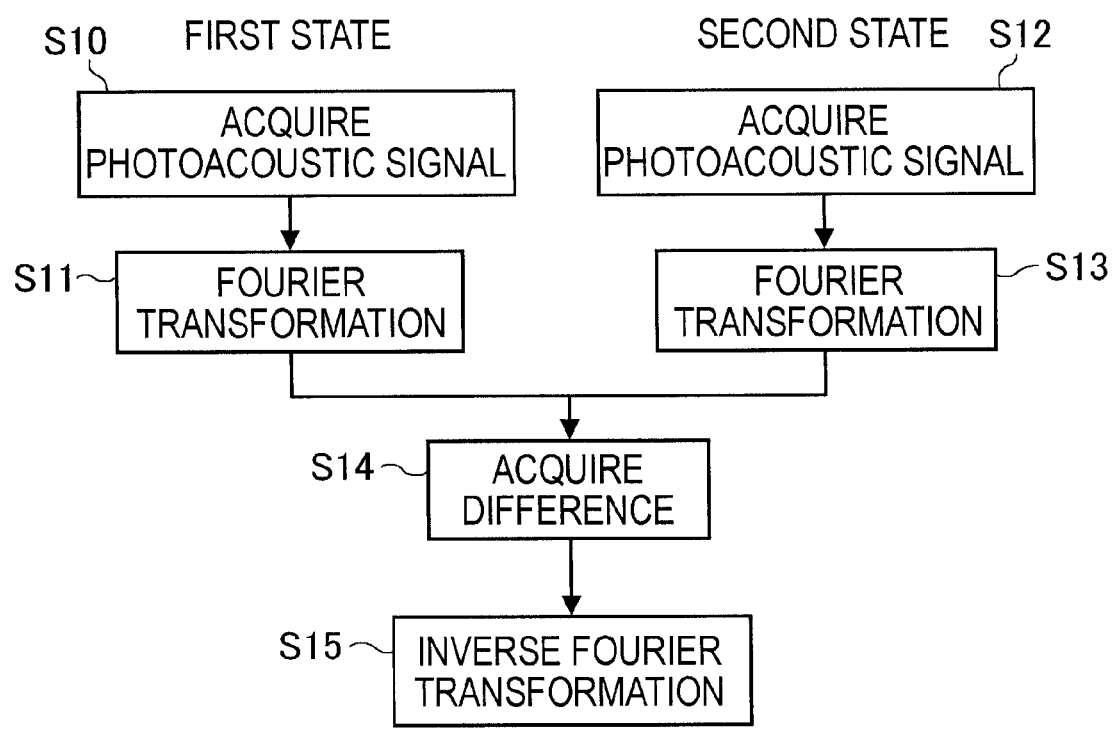

(DIFFERENCE)

BIOLOGICAL INFORMATION IMAGING APPARATUS AND BIOLOGICAL INFORMATION IMAGING METHOD

BACKGROUND OF THE INVENTION

1. Field of the Invention

The present invention relates to a biological information imaging apparatus and a biological information imaging method.

2. Description of the Related Art

Many imaging apparatuses using X-rays, ultrasonic waves, MRI (Magnetic Resonance Imaging), or the like are adopted as apparatuses acquiring biological information in a medical field, and are used for diagnosis.

With respect to an ultrasonic diagnostic imaging apparatus among these, Japanese patent application laid-open No. S62-189054 describes a method of diagnosing the heart, etc., using difference images of ultrasonic tomographic images that are taken at a high frame rate. The apparatus of this Japanese patent application laid-open No. S62-189054 once stores in a memory a plurality of time series tomographic images that are acquired by means of a probe by transmitting and receiving ultrasonic waves to and from a sample or object to be inspected, generates a difference image by subtracting the corresponding pixels of tomographic images for two frames sequentially stored, and displays the difference image thus generated on a screen.

SUMMARY OF THE INVENTION

In an ultrasonic diagnostic imaging apparatus, it is difficult to acquire a difference image in an entire region of a range (a part to be diagnosed) in which a diagnosis is intended to be made, due to the principles of diagnosis by means of ultrasonic waves. That is, in an ultrasonic diagnostic imaging apparatus, first of all, an operator sets up an ultrasonic transmission/reception direction towards a part the condition of which is to be diagnosed, such as for example a moving tissue part in a sample such as a heart, a blood vessel, etc., or a part having a blood flow, and places an ultrasonic probe in abutment with the sample. Then, ultrasonic wave pulses are transmitted from the ultrasonic probe to the interior of the sample. The ultrasonic wave propagated into the sample is reflected on a boundary where the acoustic impedance in the sample varies. The reflected wave (echo) is received by the ultrasonic probe. The echo thus received by this probe is subjected to various processing such as amplification, phasing, detection, etc., by means of a reception circuit, and then, it is digitally converted by an analog/digital converter, and stored into one of line memories in a buffer memory circuit. As a result, data for one line of ultrasonic scanning is stored in the buffer memory circuit.

Subsequently, a CPU controls a transmission circuit so that an ultrasonic wave is transmitted in a direction different from that of a first transmission/reception wave, e.g., a direction contiguous to the first transmission/reception wave direction. An echo is taken in by making its direction of reception identical to that of this transmission/reception. In synchronization with this second transmission/reception, a first echo signal is read from the buffer memory circuit, and transmitted and stored in a first image memory. On the other hand, a second echo signal is stored into the other line memory of the buffer memory circuit. Thus, the transmission and reception of an ultrasonic wave is performed by changing the direction thereof in a sequential manner, and when the scanning of one image is completed, the transmission/reception direction is returned to the initial direction, and the transmission/reception of an ultrasonic wave are carried out in a repeated manner. Then, a plurality of tomographic images are taken in a manner like a first image, a second image, a third image, . . . , an n-th image.

Thus, in an ultrasonic diagnostic imaging apparatus, a plurality of line images acquired in line sequential order have to be arranged in order to form one tomographic image. That is, a tomographic image obtained by the ultrasonic diagnostic imaging apparatus does not correctly represent the shape of a certain momentary image, but becomes an image containing a shape distortion resulting from the difference in acquisition time of the line images. For example, in cases where a tomographic image of moving tissue such as a heart is acquired, there arises a shift or difference in phase of a motion on the right and the left of the tomographic image. Accordingly, in conventional ultrasonic images, a comparison in image shape between the images of different frames has not been able to be correctly made.

In view of the aforementioned problems, the present invention has for its object to provide a biological information imaging apparatus and a biological information imaging method which are capable of performing comparison between images of different frames in a correct manner.

The present invention in a first aspect provides a biological information imaging apparatus comprising: a measurement unit that measures an acoustic wave emitted from a tissue in a living body at a time when the tissue absorbs light irradiated onto the living body; a storage unit that stores first information obtained in a first measurement by the measurement unit; and an information processing unit that generate an image of information of the tissue in the living body by using second information obtained in a second measurement by the measurement unit and the first information stored in the storage unit.

The present invention in a second aspect provides a biological information imaging method comprising: a first measurement step to measures an acoustic wave emitted from a tissue in a living body at a time when the tissue absorbs light irradiated onto the living body; a storage step to store first information obtained in the first measurement step; a second measurement step to measures an acoustic wave emitted from the tissue in the living body at a time when the tissue absorbs light irradiated onto the living body; and a processing step to generate an image of information of the tissue in the living body by using second information obtained in the second measurement step and the first information stored in the storage step.

According to the present invention, a comparison between images of different frames can be performed in a correct manner. By doing so, it becomes possible to correctly catch a change of a moving tissue, such as a motion of visceral including a heart, a change in thickness or size of a blood vessel due to a blood flow, etc.

Further features of the present invention will become apparent from the following description of exemplary embodiments with reference to the attached drawings.

BRIEF DESCRIPTION OF THE DRAWINGS

FIG. 8 is a flow chart of a third example.

DESCRIPTION OF THE EMBODIMENTS

Figure 1:
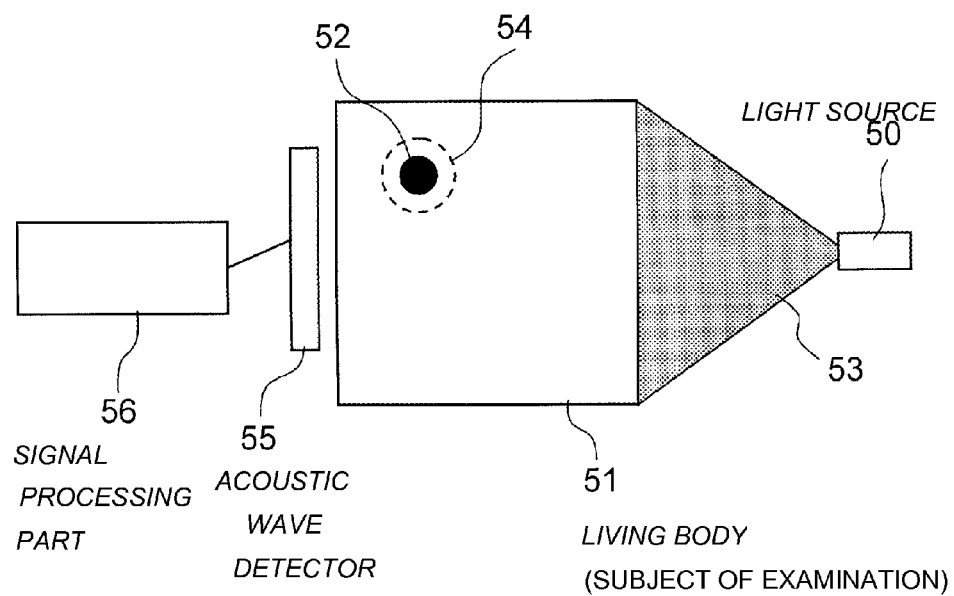
FIG. 1 is a view showing the construction of a biological information imaging apparatus in an embodiment of the present invention.

The present invention provides a biological information imaging apparatus that is constructed in the following manner.

The biological information imaging apparatus of the present invention is a biological information imaging apparatus using a photo acoustic tomography (PAT). This biological information imaging apparatus is provided with a measurement unit that measures an acoustic wave emitted from a tissue in a living body at a time when the tissue absorbs light irradiated onto the living body. The measurement unit comprises, for example, a light source, and an acoustic wave detector that detects acoustic waves (elastic waves, ultrasonic waves) generated from a light absorber (optical absorber) which has absorbed a part of the energy of light irradiated to the living body, and transduces them into electric signals. In addition, the biological information imaging apparatus is provided with a storage unit (memory) that stores first information acquired in a first measurement by the measurement unit. It is desirable that the storage unit have a capacity capable of storing the information acquired in at least one measurement (e.g., a reconstructed image for one frame). Also, the biological information imaging apparatus is provided with an information processing unit, and this information processing unit generates an image of the information of the tissue in the living body by using second information acquired in a second measurement by the measurement unit and the first information stored in the storage unit. Specifically, the second measurement is carried out at a timing at which the shape of the tissue is different from that at the timing of the first measurement, and the information processing unit generates a difference image representing a difference between the first information and the second information. Here, "the shape of the tissue is different" means that at least either of the shape, position and size of the tissue differs. The tissue, which is a target of imaging, is a blood vessel, for example.

(Basic Principles of PAT)

PAT is a technique that irradiates a living body with pulsed light generated from a light source, detects acoustic waves emitted from a living tissue which absorbed the energy of the light propagated and diffused in the living body, and performs analytic processing of their signals. With this technology, because of the use of light, it can be found how the light is absorbed in the living tissue, and at the same time, because of performing detection by acoustic waves (elastic waves, typically ultrasonic waves), an optical property distribution in the living body can be obtained at a resolution substantially equivalent to that in an ultrasonic diagnostic imaging apparatus.

In PAT, a sound pressure P of the acoustic waves obtained from a light absorber in the living body due to the light absorption is given by the following formula (1).

$$P = \Gamma \cdot \mu_a \cdot \Phi \quad (1)$$

Here $\Gamma$ is a Grüneisen parameter which is an elastic property value, and which is obtained by dividing the product of a volume expansion coefficient $\beta$ and the square of a speed of sound c by a specific heat $C_P$. In addition, $\mu_a$ is an optical absorption coefficient of the absorber, and $\Phi$ is a quantity of light in a local region (a quantity of localized light irradiated to the absorber).

Since it is known that $\Gamma$ will take an almost constant value if the tissue is decided, the product of $\mu_a$ and $\Phi$, i.e., an optical energy absorption density, can be estimated by measuring the sound pressure P, which is the magnitude of the acoustic waves, in a time sharing manner. In addition, by measuring this at multipoints, a spatial distribution of the absorber in the living body can be acquired.

The basic principle of image picking-up by the PAT technique is briefly as follows.

(1) A sample is irradiated with light from the outside thereof.
(2) The light propagates through the interior of the sample.
(3) A part (light absorber) of a large optical absorption coefficient existing in the interior of the sample absorbs the light.
(4) The part concerned is heated due to the above-mentioned optical absorption.
(5) The part thus heated expands.
(6) An acoustic wave (ultrasonic wave) is generated (emitted) in accordance with the expansion of the heated part.
(7) The acoustic wave propagates through the interior of the sample.
(8) The propagating acoustic wave is received by the use of an acoustic wave detector (an ultrasonic probe).
(9) Time difference of the arrival acoustic wave, etc., is analyzed to reconstruct tomographic images or three-dimensional images of the sample.

As stated in the above-mentioned problems, one frame period is required for the conventional ultrasonic diagnostic imaging apparatus to form one image. That is, in general, in cases where a video of 30 frames per second is displayed, images at time points different by 1/30 second from each other will be displayed at the first line and the last line, respectively, in one frame.

On the other hand, in cases where the PAT technique is used, ultrasonic waves can be simultaneously generated from a desired diagnostic region by irradiating it with light. For example, if the diagnostic region is a square area with each side of 10 centimeter, the arrival time differences of the light are about a maximum of 0.3 pico seconds. This is equivalent to an error of 0.5 micrometers when it is assumed that the propagation speed of ultrasonic waves in the living body is 1,500 meters per second. In view of the fact that the resolution required in the PAT technique is on the order of from submillimeters to several millimeters, such an error can be completely disregarded. That is, in the PAT technique, it is possible to acquire an image (image shape) at substantially the same time.

(Example of the Construction of the Biological Information Imaging Apparatus)

FIG. 1 shows a view explaining an example of the construction of the biological information imaging apparatus in this embodiment. The biological information imaging apparatus is provided with a light source (including an optical control part) 50, an acoustic wave detector 55, and a signal processing part (information processing unit) 56.

The light source 50 is a unit for irradiating a living body 51 with pulsed light 53. An optical waveguide such as an optical fiber for guiding the light to the living body 51 may be provided as needed. The light source 50 irradiates light of a specific wave length that can be absorbed by a specific component existing in the living body. As the light source, there is provided at least one pulsed light source that can generate pulsed light on the order of from several to hundreds nanoseconds. A laser is desirable as the light source, but it is also possible to use a light emitting diode or the like instead of the laser. As a laser, there can be used various kinds of laser such as a solid-state laser, a gas laser, a dye laser, a semiconductor laser, and so on. In addition, although in this embodiment, an example of a single light source is shown, a plurality of light sources can be used. In the case of the plurality of light sources, in order to raise the irradiation intensity of the light to be irradiated on the living body, there can be used two or more light sources which oscillate at the same wave length, or in order to measure differences in the optical property value distribution according to the wave lengths, two or more light sources having different oscillation wavelengths can be used. Here, note that if a dye of which the oscillating wave length is convertible and OPO (Optical Parametric Oscillators) can be used as the light source, it will also become possible to measure the difference in the optical property value distributions depending upon the wave lengths. It is preferable that the wave lengths to be used be in a range of from 700 to 1,100 nm in which there is little absorption in the living body. However, in cases where an optical property value distribution of the living body tissue relatively near a living body surface thereof, it is also possible to use a wave length range, such as for example a range of from 400 to 1,600 nm, wider than the above-mentioned wavelength range.

The acoustic wave detector 55 is a unit for detecting an acoustic wave 54 emitted from the light absorber 52 which absorbed a part of the energy of light irradiated to the living body 51, and transducing (changing) it into an electric signal. The electric signal outputted from the acoustic wave detector 55 is inputted into the signal processing part 56. As the acoustic wave detector 55, there can be used a transducer using a piezo-electric phenomenon, a transducer using the resonance of light, a transducer using a change of capacitance, and so on. As the light absorber 52, it corresponds, for example, to a blood vessel, a tumor, or like other tissues similar to these. Here, note that this embodiment is suitable in particular for imaging a light absorber in motion.

The signal processing part 56 is a function to analyze the electric signal outputted from the acoustic wave detector 55, and to obtain optical property value distribution information on the living body. In addition, the signal processing part 56 has an image memory (frame memory) that stores image information (image data of tomographic images or three dimensional images) for at least one screen. Moreover, the signal processing part 56 also has a function to compare a first image acquired in a first state at one timing and stored in this image memory with a second image acquired in a second state at another timing, and to calculate a difference between them. The signal processing part 56 can also take any construction and arrangement as long as functions, such as inputting of electric signals, storage and operation of data (including image information), outputting of the results of the operation, and so on, can be achieved. For example, the signal processing part 56 can be comprised of a computer with an analysis program. Here, note that the optical property value distribution information, the difference image information, etc., which are the results of operations of the signal processing part 56, are outputted to a display device (not shown).

(Generation Processing of the Difference Image)

The image picking-up by the PAT technique in this embodiment is performed in the following flow. Here, note that a mechanism in which acoustic waves are emitted from the light absorber by irradiation of light is the same as that in the flow of the basic principle as mentioned above.

(1) Light is irradiated to the sample in its first state from the outside thereof.
(2) A first acoustic wave (ultrasonic wave) is emitted from a part having a large optical absorption coefficient.
(3) The first acoustic wave having propagated through the interior of the sample is received by the use of the acoustic wave detector (the ultrasonic probe) in the outside of the sample (a first measurement step).
(4) The time difference of the arrival acoustic wave, etc., is analyzed and the first image (tomographic image or three-dimensional image) of the sample is reconstructed.
(5) The first image thus acquired is stored in the image memory (a storage step).
(6) Light is irradiated to the sample from the outside thereof in its second state different from the first state.
(7) A second acoustic wave (ultrasonic wave) is emitted from the part having the large optical absorption coefficient.
(8) The second acoustic wave having propagated through the interior of the sample is received by the use of the acoustic wave detector (the ultrasonic probe) in the outside of the sample (a second measurement step).
(9) The time difference of the arrival acoustic wave, etc., is analyzed and the second image (tomographic image or three-dimensional image) of the sample is reconstructed.
(10) A difference is acquired by comparing the second image acquired in (9) with the first image stored in the image memory in (5) (a processing step).

According to the above-mentioned flow, after performing the first measurement and the second measurement at different timings and reconstructing the images in the two different states, it is possible to extract only those parts which have changed by acquiring the difference between these two images. Here, note that the first measurement and the second measurement are performed at timings at which tissues (a blood vessel, a lesion part, etc.) to be measured are mutually different in shape from each other.

(Advantages of the Embodiment)

According to this embodiment of the present invention as described above, a comparison between frames becomes able to be correctly made, so it is possible to extract only those parts which are changing by acquiring the difference between the frames. That is, in the conventional ultrasonic diagnostic apparatus which acquires an image in line sequential order, it is impossible to make a comparison between frames in a correct manner as shown in the aforementioned problems, but in contrast, with the construction of this embodiment, photoacoustic tomography is used upon imaging. Since this method performs imaging by irradiating light without scanning in a line sequential fashion unlike the conventional ultrasonic diagnostic imaging apparatus, it becomes possible to acquire simultaneous information on different places inside the living body. As a result, it becomes possible from the difference images between the frames to grasp how the state of the tissue changes in a correct manner. By making use of this, it will become possible to take a vivid or clear image of a moving tissue such as for example a blood vessel figure, a lesion part that has changed over time, etc.

First Example

A first example of the present invention will be described below.

The first example is an example in which image reconstruction is carried out from ultrasonic waves detected in the entire circumference of the sample. Here, reference will be made to a simulation that was performed under the condition that a situation at the time of actual measurement is simulated while using drawings. Although a three-dimensional space has to be taken into consideration in actual measurement or diagnosis, computations on a two-dimensional plane are shown in this computation process.

Figure 2A:
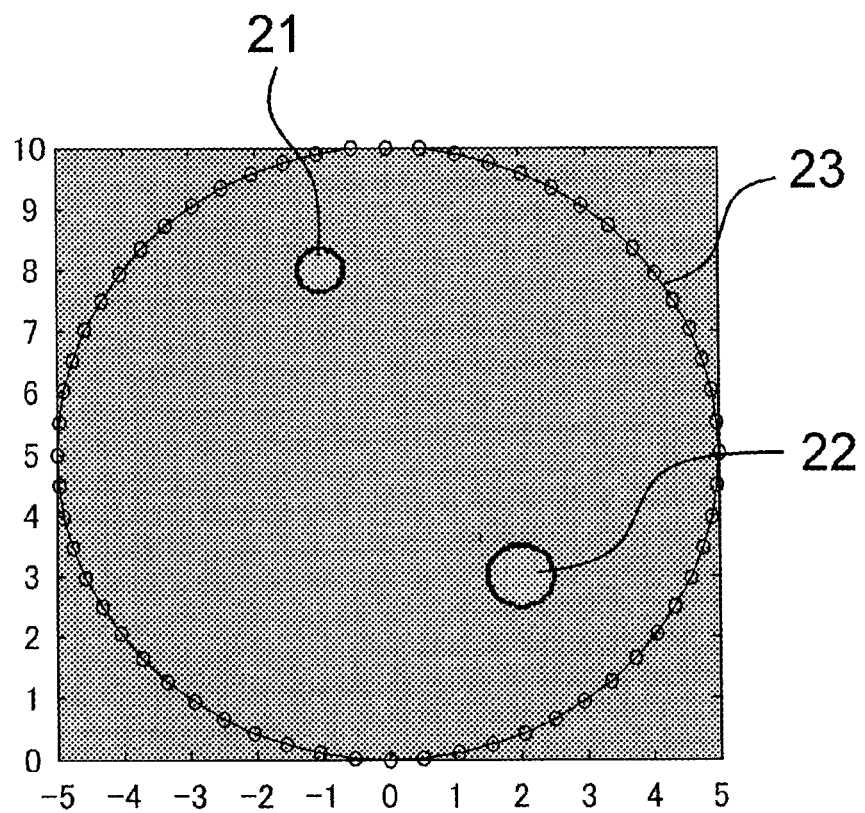
FIG. 2A is a view showing the arrangement of a sample in a first state in the first example.
Figure 3A:
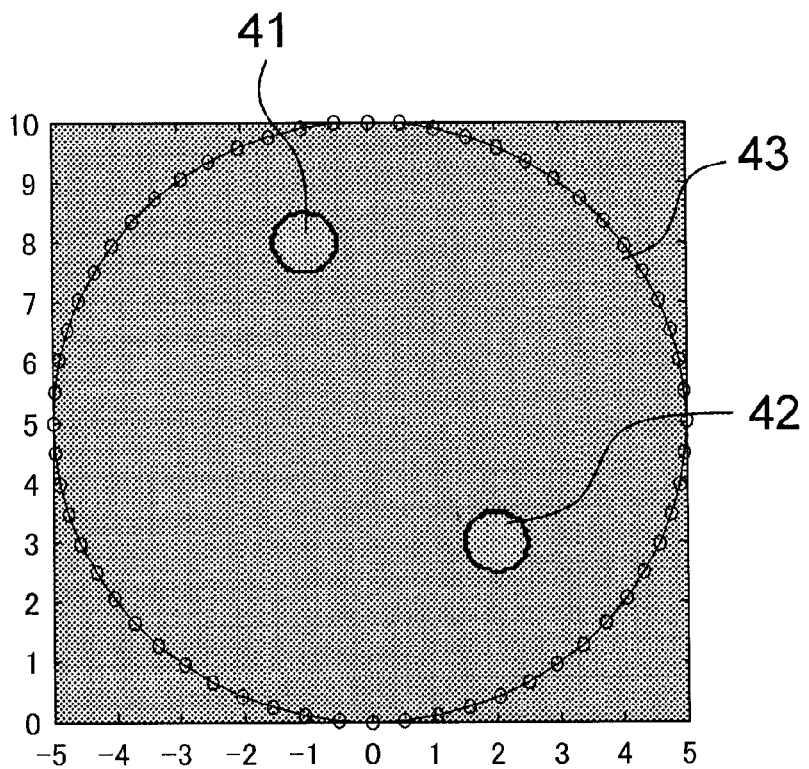
FIG. 3A is a view showing the arrangement of the sample in a second state in the first example.

FIG. 2A and FIG. 3A illustrate implementation conditions for the simulation employed in the first example, and indicate an arrangement of the sample. FIG. 2A indicates a first state and FIG. 3A indicates a second state. Here, for example, in FIG. 2A, reference numerals 21 and 22 denote light absorbers, respectively. Uniform light is irradiated to this sample from an arbitrary place (not shown), so that acoustic waves emitted from the light absorbers 21, 22 are detected by an ultrasonic probe 23 which is an acoustic wave detector. This ultrasonic probe 23 takes a substantially circular shape that encloses the entire circumferences of the light absorbers 21, 22. Sixty small circles drawn on the circle indicate ultrasonic wave receiving elements, respectively. That is, the ultrasonic waves emitted from the light absorbers 21, 22 are detected by the sixty ultrasonic wave receiving elements that are arranged on the entire circumference. In FIG. 3A, reference numerals 41 and 42 denote light absorbers, respectively, and a reference numeral 43 denotes an ultrasonic probe. A difference between FIG. 2A and FIG. 3A is that the shapes of the light absorbers (21, 41) lying in the upper left in these figures are different from each other.

It is known that, as for an acoustic wave generated due to an photoacoustic effect, an acoustic wave emitted from an absorber, if its shape is spherical, can be analytically calculated through calculation, and that the acoustic wave thus calculated is in match with that obtained through experiments. In a calculation limited on a two-dimensional plane, if the shape of an absorber is circular, an acoustic wave emitted from the absorber can be calculated in a similar manner. That is, it is known that the profile of the ultrasonic wave exhibits a change of "N" shape in which the change of its amplitude once rises from zero to a positive pressure, then falls to a negative pressure, and thereafter returns to zero. It is also known that the width of this N shape is proportional to the size of the light absorber, and that the height (amplitude) of the N shape is proportional to the product of an amount of light arrived and an optical absorption coefficient, as shown by the above-mentioned formula (1).

Figure 2B:
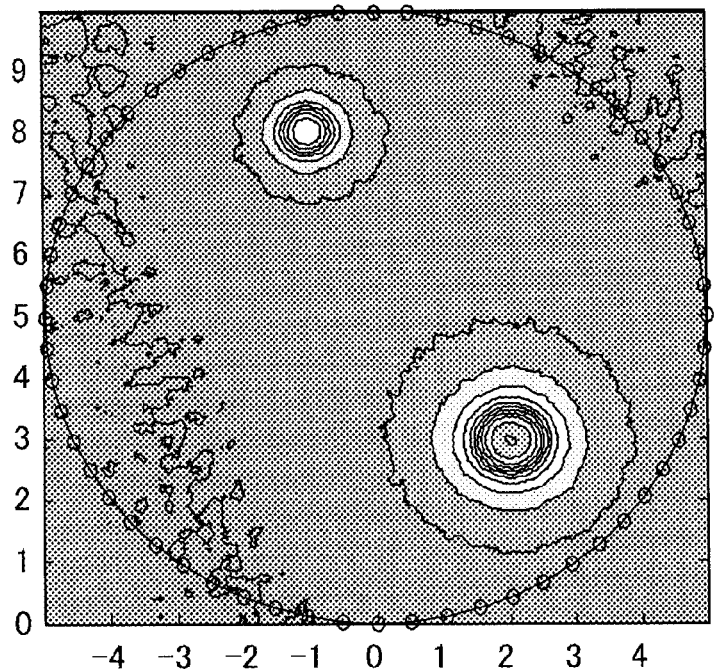
FIG. 2B is a view showing a reconstructed image in the first state.
Figure 3B:
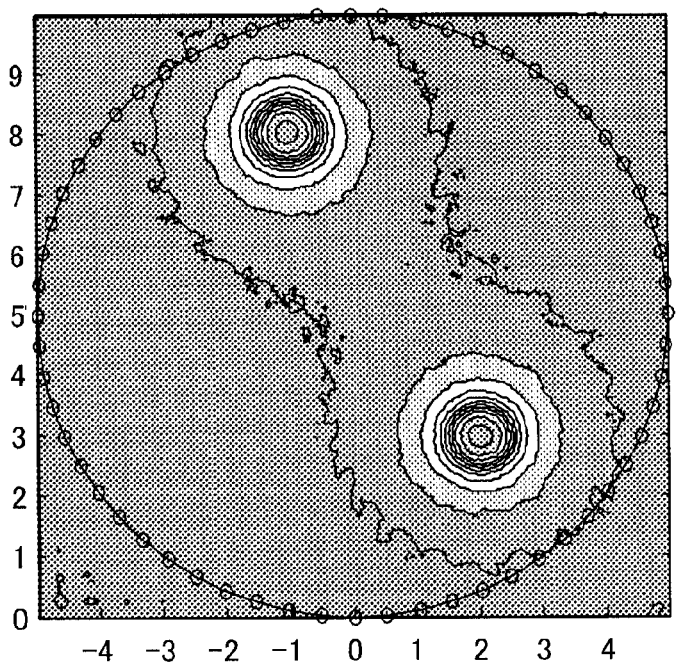
FIG. 3B is a view showing the reconstructed image in the second state.

The acoustic waves generated in the light absorbers spread in an isotropic manner, propagate through the interior of the living body, and arrive at the ultrasonic wave receiving elements. The arrival acoustic waves, which have been measured at a plurality of points, can be imaged by using a well-known analysis method. In this example, image reconstruction was performed using a well-known circular back projection method (CBP method), and a first image was obtained from acoustic wave signals detected at sixty points in the sample of FIG. 2A. FIG. 2B shows the first image. On the other hand, image reconstruction was performed with the sample of FIG. 3A as in the case of FIG. 2A, whereby a second image was obtained. FIG. 3B shows the second image.

Even if the image of FIG. 2B and the image of FIG. 3B are juxtaposed and compared with each other, two circular-shaped things only exist in both of these images, so it is difficult to distinguish differences between these two images immediately.

Figure 4:
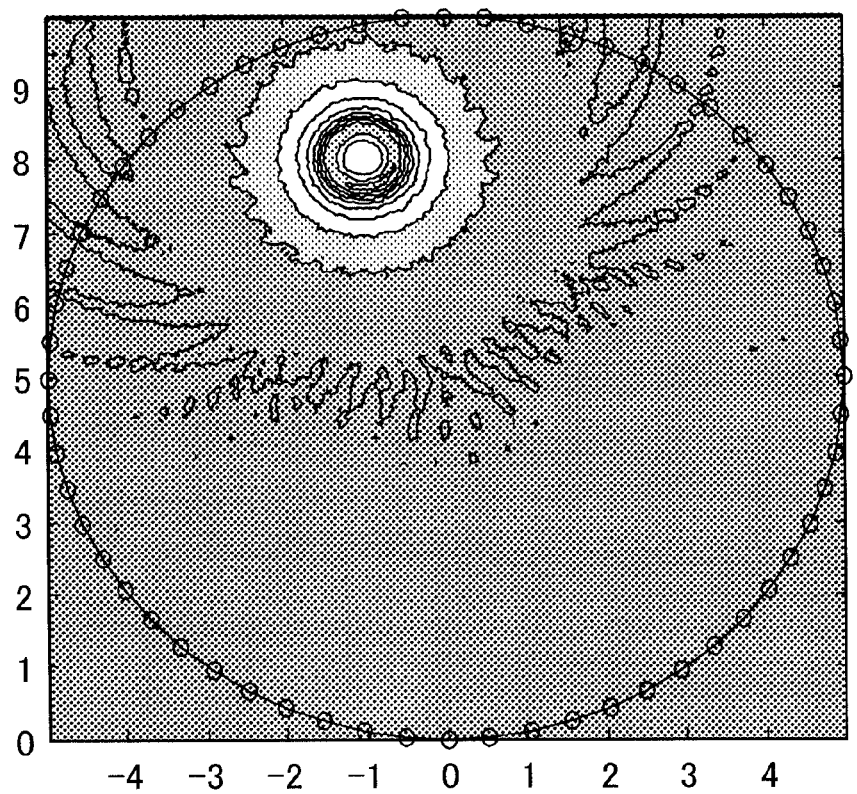
FIG. 4 is a view showing a difference image between the images in the first state and the second state in the first example.

Accordingly, in this example, a difference between the image of FIG. 2B and the image of FIG. 3B (a density difference between pixels) is calculated, and a difference image thus obtained is outputted. FIG. 4 shows the difference image. In the difference image, parts of an identical shape (light absorbers 22, 42) are eliminated, and parts of different shapes (light absorbers 21, 41) are extracted. Thus, by calculating a difference between two images acquired in their different states, it becomes possible to obtain an image in which only those parts of which the shapes, the positions, the sizes, etc., are changing are emphasized.

Second Example

A second example of the present invention will be described below.

The second example is an example in which image reconstruction is carried out from ultrasonic waves detected at one side of a sample. That is, in the first example, the ultrasonic wave receiving elements are arranged so as to surround the two light absorbers, but in contrast, in the second example, ultrasonic wave receiving elements are arranged only at one side with respect to a light absorber. Here, reference will be made to a simulation that was performed under the condition that a situation at the time of actual measurement is simulated while using drawings. Although a three-dimensional space has to be taken into consideration in actual measurement or diagnosis, computations on a two-dimensional plane are shown in this computation process.

Figure 5A:
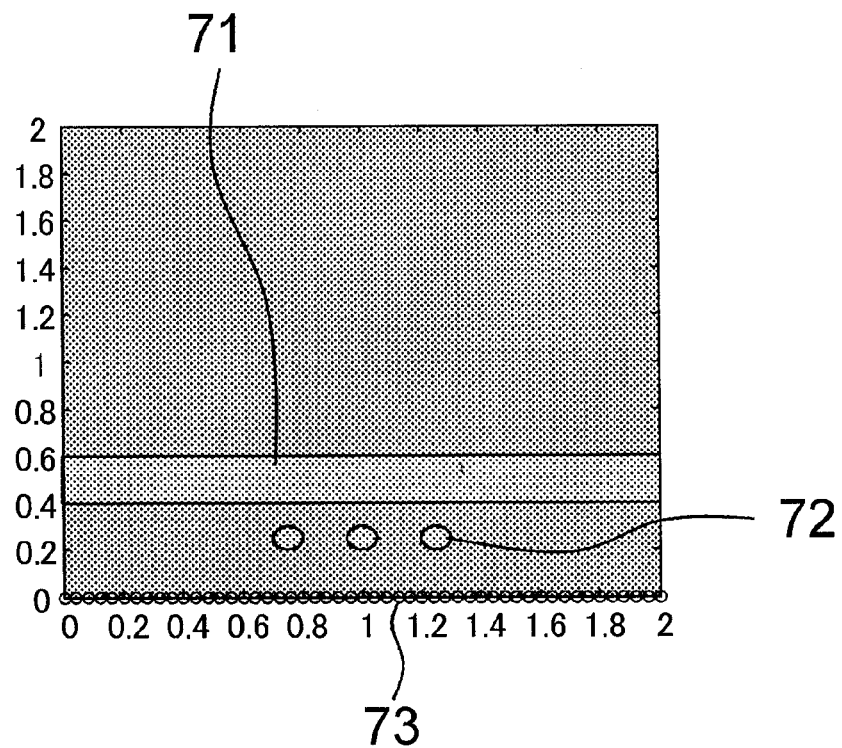
FIG. 5A is a view showing the arrangement of a sample in a first state in a second example.
Figure 6A:
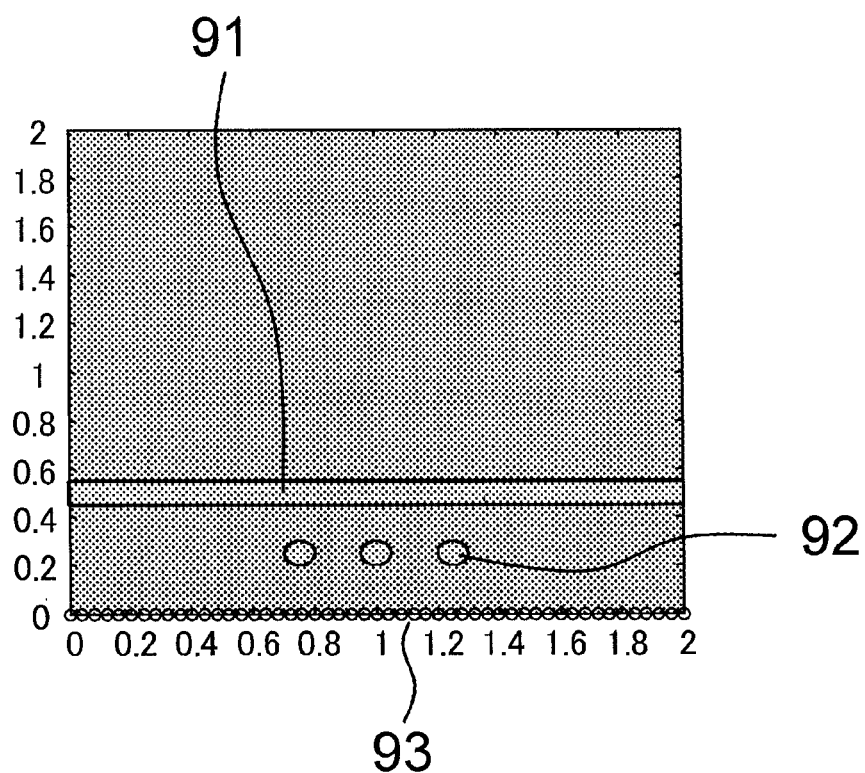
FIG. 6A is a view showing the arrangement of the sample in a second state in the second example.

FIG. 5A and FIG. 6A indicate the arrangements of the sample used for the second example. FIG. 5A indicates a first state of the sample, and FIG. 6A indicates a second state thereof. Here, in FIG. 5A, a reference numeral 71 denotes a light absorber of a rod shape, and a reference numeral 72 denotes light absorbers each of a circular shape. These light absorbers are irradiated with uniform light from arbitrary places (not shown), and acoustic waves emitted from the light absorbers 71, 72 are detected by an ultrasonic probe 73 which is an acoustic wave detector. Here, note that a difference between FIG. 5A and FIG. 6A is that the sizes of rod-shaped light absorbers (71, 91) are different from each other. The diameters of circular-shaped light absorbers (72, 92) are the same.

Figure 5B:
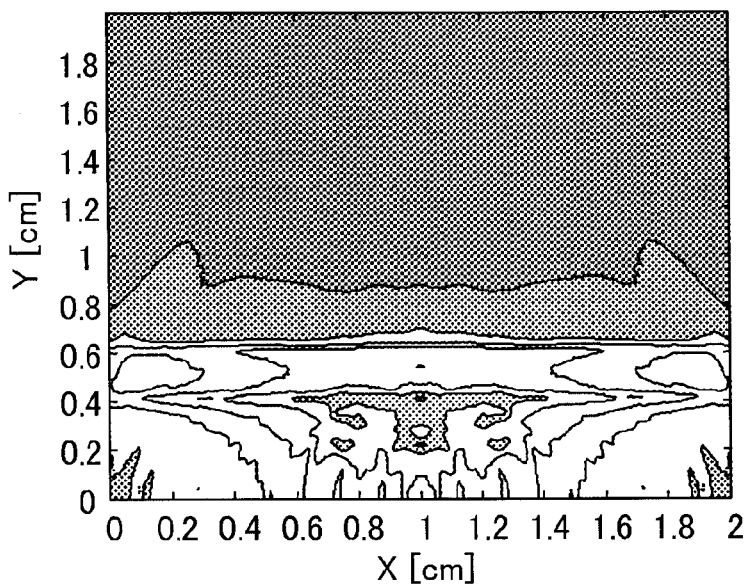
FIG. 5B is a view showing a reconstructed image in the first state.

In such arrangements, image reconstruction was carried out by using the CBP method, as in the first example. The first image, which is the result reconstructed from ultrasonic signals detected in the sample arrangement of FIG. 5A is shown in FIG. 5B. Also, the second image, which is the result reconstructed from ultrasonic signals detected in the sample arrangement of FIG. 6A is shown in FIG. 6B.

Figure 6B:
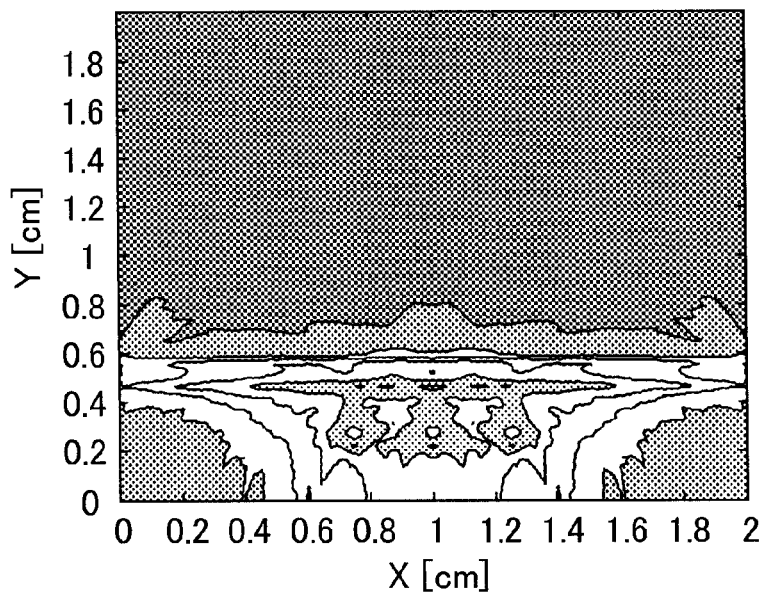
FIG. 6B is a view showing a reconstructed image in the second state.

Thus, in both FIG. 5B and FIG. 6B, parts of reconstructed images of the rod-shaped light absorber and the circular-shaped light absorbers overlap with one another, and good reconstructed images can not be obtained. As a result, it is difficult to distinguish the difference in size of the rod-shaped light absorbers.

Figure 7:
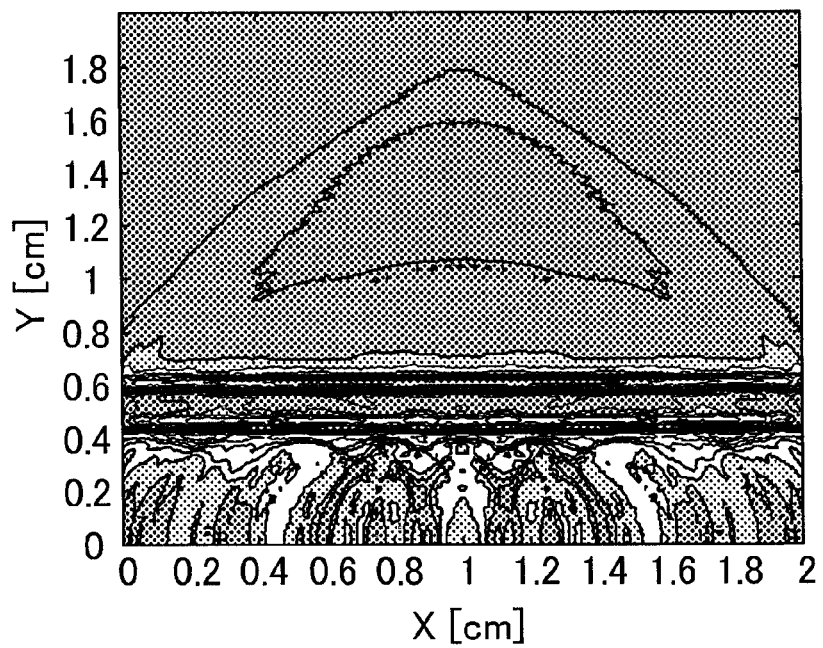
FIG. 7 is a view showing a difference image between the images in the first state and the second state in the second example.

In contrast to these, FIG. 7 shows that differences between these image data are calculated. In FIG. 7, the image of a circular-shaped light absorber is eliminated by means of difference calculation between the image data. Although the image is disturbed a little due to the influence of the rod-shaped light absorber and the shortage in the amount of information resulting from receiving the ultrasonic signals only at one side of the rod-shaped light absorber, it is understood that a rod-shaped part, being different in shape from others, has been extracted. Thus, by calculating a difference between two images acquired in their different states, it becomes possible to obtain an image in which only those parts of which the shapes, the positions, the sizes, etc., are changing are emphasized.

Third Example

A third example of the present invention will be described below.

In the first and second examples, those parts which have changed in their state are extracted by generating a difference image between image data after performing image reconstruction. That is, difference calculation is performed in real space. In contrast to this, in the third example, a difference image is generated from data that is obtained by transforming acoustic wave signals into corresponding signals in a frequency domain, taking a difference between signal data in the frequency domain, and performing inverse transformation of the difference to a space domain.

FIG. 8 is a flow chart which shows the flow of processing of the third example. First, in the first state, light irradiation and acoustic wave detection are performed (step S10), and the thus detected acoustic wave signals are Fourier-transformed (step S11). The Fourier-transformed signal data for one image are stored in the image memory. Then, in the second state, light irradiation and acoustic wave detection are performed (step S12), and the thus detected acoustic wave signals are Fourier-transformed (step S13). Thereafter, a difference between the signal data acquired in the first state and the signal data acquired in the second state is taken (step S14), and inverse Fourier transformation of the difference data is carried out (step S15). Image reconstruction is performed from the difference data of the acoustic wave signals obtained by the inverse Fourier transformation.

Figure 9A:
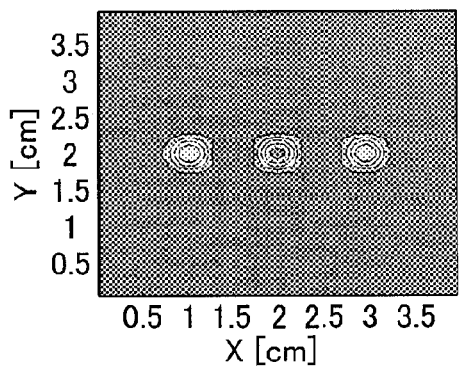
FIG. 9A is a view showing a reconstructed image in a first state in the third example.
Figure 9B:
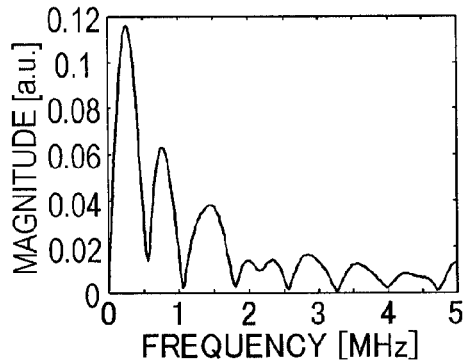
FIG. 9B is a view showing Fourier transformation data for the image in the first state.
Figure 9C:
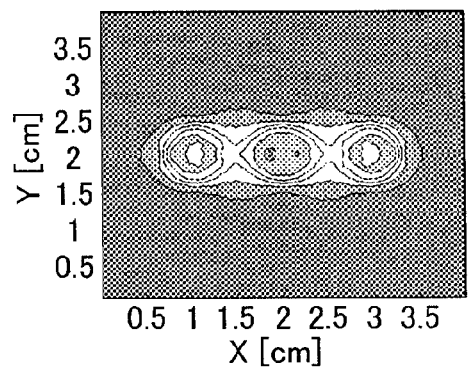
FIG. 9C is a view showing a reconstructed image in a second state.
Figure 9D:
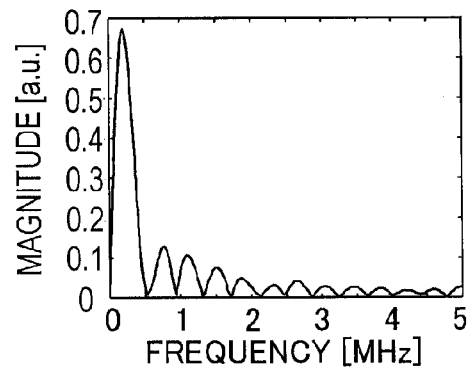
FIG. 9D is a view showing Fourier transformation data for the image in the second state.

Hereafter, the result of a simulation of the third example will be explained by using FIG. 9A through FIG. 9F. In the third example, there is employed a sample in which three light absorbers each of a circular shape are arranged at intervals of 1 cm at locations apart by 2 cm from an ultrasonic probe. FIG. 9A shows an image reconstructed from the acoustic wave signals acquired in the first state, and FIG. 9B shows the data obtained by Fourier-transforming the acoustic wave signals acquired in the first state. In addition, FIG. 9C shows an image reconstructed from the acoustic wave signals acquired in the second state, and FIG. 9D shows the data obtained by Fourier-transforming the acoustic wave signals acquired in the second state. A difference between the first state and the second state is that in the first state, the diameter of each light absorber is 2 mm, whereas in the second state, the diameter of each light absorber is 4 mm.

Figure 9E:
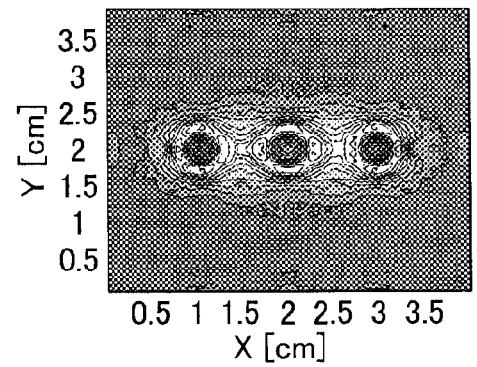
FIG. 9E is a view showing an image which is obtained by performing inverse Fourier transform on difference data.
Figure 9F:
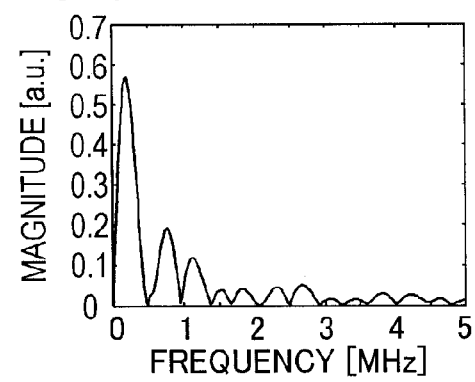
FIG. 9F is a view showing the difference data between the images in the first and second state.

FIG. 9F shows the difference data between the signal data shown in FIG. 9B and the signal data shown in FIG. 9D. FIG. 9E shows what was obtained by imaging the difference data of FIG. 9F through inverse Fourier transformation. Thus, even if the difference is acquired in a frequency space, it is possible to extract those parts which have been changed in their states.

Other Examples

Figure 10:
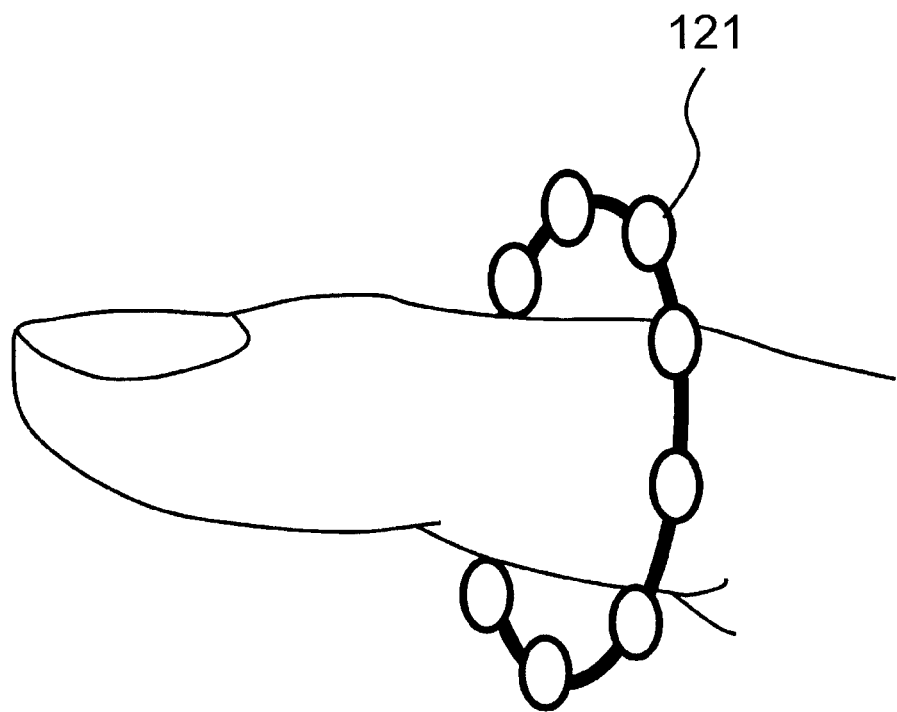
FIG. 10 is a view showing an example in which an ultrasonic probe is arranged around an entire circumference of a living body.
Figure 11:
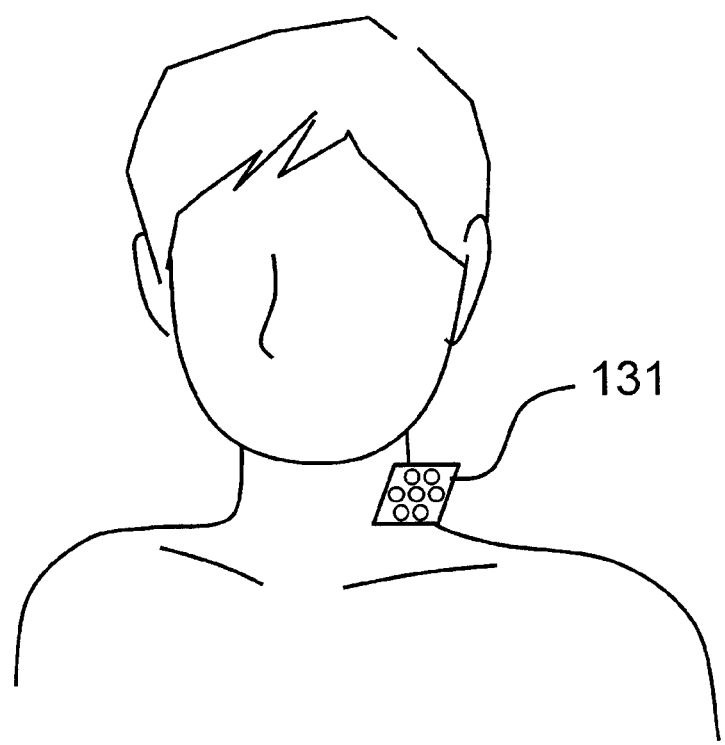
FIG. 11 is a view showing an example in which an ultrasonic probe is arranged at one side of a living body.

A blood vessel can be imaged by using the methods according to the above-mentioned examples. For example, the method of the first example can be used in cases where an ultrasonic probe 121 is arranged around a finger for measuring ultrasonic waves, as shown in FIG. 10. Also, the method of the second example can be used in cases where an ultrasonic probe 131 is arranged at one side face with respect to a blood vessel in such a manner as to be pressed against a carotid artery for measuring ultrasonic waves, for example, as shown in FIG. 11.

Here, note that, in either of the above cases, it is desirable to use a matching agent or the like which is arranged between the ultrasonic probe and the living body for taking the matching of acoustic impedance therebetween.

The blood vessel is momentarily changing its size in accordance with the flow of blood therein. That is, the blood vessel contracts and expands its size to cause blood to flow therein in synchronization with the heartbeat. Thus, the biological information imaging apparatus monitors the heart beat, and performs light irradiation in synchronization with the heart beat, whereby it becomes possible for the apparatus to acquire the state at that timing as an image. Specifically, when blood pressure is substantially systolic blood pressure (first state), a first measurement is carried out, and when the blood pressure is substantially diastolic blood pressure (second state), a second measurement is carried out. Thereby, an image of the blood vessel in a high blood pressure state and an image of the blood vessel in a low blood pressure state are obtained. Then, by performing a comparison between these images, it becomes possible to represent only those parts in which the diameter of the blood vessel has changed following the blood pressure change.

Now, in cases where a part in which the heart beat is measured and a part which is to be diagnosed are separated from each other, a synchronized image can not necessarily be obtained. In this case, if a measurement is made in a rest state as the first state and a measurement is then made in a high heart rate as the second state, a blood vessel figure can be imaged in a correct manner. That is, the timing at which the size of a blood vessel in the first state coincides with that in the second state in which the heart rate is different from that in the first state is very rare, and hence, if a difference is taken between such states, it will become possible to image the blood vessel. In cases where such a difference can not be taken well, the probability at which the blood vessel can be imaged well will be increased if a measurement is performed again in a high heart rate state.

Here, note that, in order to create these two states, a state in which the measurement is carried out after one takes a rest such as sleeping on a bed or sitting on a chair is made the first state, and a state in which the measurement is carried out after one is put into a high heart rate state by doing exercise spontaneously or by being given a stimulus or stress from the outside is made the second state. Thus, the blood vessel can be imaged from a difference image between the two states.

Alternatively, a device with a function to cause such a high heart rate state (e.g., a stress applying function) may also be built into the above-mentioned biological information imaging apparatus. In addition, the biological information imaging apparatus may have a function to measure the heart rate, so that it can automatically determine whether one is in a high heart rate state, and decide the timing at which a second measurement is made.

In addition, a compare may be made between different blood pressure states. For example, an early morning hypotensive state is assumed to be the first state, and a measurement at this time is assumed as the first measurement. Subsequently, a high blood pressure state in an active time zone is assumed to be the second state, and a measurement at this time is assumed as the second measurement. By acquiring a difference between these two states, it becomes possible to image a blood vessel. Also, the biological information imaging apparatus may have a function to measure the blood pressure, so that it can automatically determine whether one is in a low blood pressure state or in a high blood pressure state.

Moreover, it is known that a difference between tissues can be observed by using two kinds of light of different wave lengths. For example, since the degree of oxidation of hemoglobin changes with the wave length of light, it is known that an artery and a vein can be imaged by performing measurements while changing the wave length of light.

When imaging the above-mentioned blood vessels, the change in the size of the blood vessel in the artery is large, whereas in the vein, the size of its blood vessel is little changed even due to the flow of blood therein. That is, it can be considered that the vein is a reference tissue of which the state does not change. By making use of this, at the time of acquiring a difference between the two states, it becomes possible to obtain a difference image with substantially no occurrence of a positional shift by performing registration in such a manner that the reference tissues, i.e., veins, of which the states do not change, are in register with each other.

In order to perform imaging according to a vein(s), imaging in the first state and imaging in the second state are carried out in a wavelength band (700 through 800 nm) in which a lot of hemoglobin uncombined with oxygen can be absorbed. Subsequently, imaging in the first state and imaging in the second state are carried out in a wavelength band (800 through 1,000 nm) in which a lot of oxygenated hemoglobin can be absorbed. The reconstruction of images thus obtained is carried out in such a manner that a reconstructed image in the wavelength band in which a lot of hemoglobin uncombined with oxygen can be absorbed is taken to be a venous image, and registration is performed in such a manner that a venous image in the first state and a venous image in the second state are in match with each other. Thereafter, in that position thus registered, a difference between the reconstructed images at the wave length at which the oxygenated hemoglobin is absorbed is acquired.

It becomes possible to image the artery in a more accurate manner by obtaining a difference image with such a procedure.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-211993, filed on Aug. 20, 2008, which is hereby incorporated by reference herein in its entirety.

What is claimed is:

1. A biological information imaging method comprising the steps of:
    irradiating a sample with light at a first timing;
    irradiating the sample with the light at a second timing which is different from the first timing;
    detecting a first acoustic wave generated in the sample by irradiating the sample with the light at the first timing and converting the first acoustic wave into a first electric signal;
    detecting a second acoustic wave generated in the sample by irradiating the sample with the light at the second timing and converting the second acoustic wave into a second electric signal;
    obtaining a first image based on the first electric signal;
    obtaining a second image based on the second electrical signal; and
    obtaining a difference image representing a difference between the first image and the second image,
    wherein the sample is irradiated with the light at the second timing when a heart rate is different from that at the first timing.

2. The biological information imaging method according to claim 1, wherein the sample is irradiated with the light at the second timing when a shape of the sample is different from that at the first timing.

3. The biological information imaging method according to claim 1, wherein the sample is a blood vessel.

4. A biological information imaging method comprising the steps of:
    irradiating a sample with light at a first timing;
    irradiating the sample with the light at a second timing which is different from the first timing;
    detecting a first acoustic wave generated in the sample by irradiating the sample with the light at the first timing and converting the first acoustic wave into a first electric signal;
    detecting a second acoustic wave generated in the sample by irradiating the sample with the light at the second timing and converting the second acoustic wave into a second electric signal;
    obtaining a first image based on the first electric signal;
    obtaining a second image based on the second electrical signal; and
    obtaining a difference image representing a difference between the first image and the second image,
    wherein the sample is irradiated with the light at the second timing when a blood pressure is different from that at the first timing.

5. The biological information imaging method according to claim 4, wherein the sample is irradiated with the light at the second timing when a shape of the sample is different from that at the first timing.

6. The biological information imaging method according to claim 4, wherein the sample is a blood vessel.

7. A biological information imaging method comprising the steps of:
    irradiating a sample with light at a first timing;
    irradiating the sample with the light at a second timing which is different from the first timing;
    detecting a first acoustic wave generated in the sample by irradiating the sample with the light at the first timing and converting the first acoustic wave into a first electric signal;
    detecting a second acoustic wave generated in the sample by irradiating the sample with the light at the second timing and converting the second acoustic wave into a second electric signal;
    obtaining a first image based on the first electric signal;
    obtaining a second image based on the second electrical signal; and obtaining a difference image representing a difference between the first image and the second image,
wherein the sample is irradiated with the light at the first timing when a blood pressure is systolic blood pressure, and is irradiated with the light at the second timing when a blood pressure is diastolic blood pressure.

8. The biological information imaging method according to claim 7, wherein the sample is irradiated with the light at the second timing when a shape of the sample is different from that at the first timing.

9. The biological information imaging method according to claim 4, wherein the sample is a blood vessel.

* * * * *